United States Patent [19]

Beavers

[11] Patent Number: 5,382,700
[45] Date of Patent: Jan. 17, 1995

[54] OXIDATIVE COUPLING OF ALPHA, BETA UNSATURATED ALDEHYDES

[75] Inventor: William A. Beavers, Longview, Tex.

[73] Assignee: Eastman Chemical Company, Kingsport, Tenn.

[21] Appl. No.: 65,557

[22] Filed: May 24, 1993

[51] Int. Cl.$^6$ ............................................. C07C 45/00
[52] U.S. Cl. .................... 568/463; 568/458; 568/459; 568/461
[58] Field of Search ................ 568/458, 463, 459, 461

[56] References Cited

U.S. PATENT DOCUMENTS 3,523,125  8/1970  Theissen ............................ 568/459

FOREIGN PATENT DOCUMENTS 580383  9/1946  United Kingdom ................ 568/461

OTHER PUBLICATIONS

Rec. Trav. Chim., 84, 1203 (1965).
Tetr., 34 641, (1978).
Org. Synth. Coll., vol. V, 517 (1973).
J. Amer. Chem. Soc., 99, 1487 (1977).
J. Org. Chem., 36, 3160 (1971).
Rec. Trav. Chim., 84, 1233 (1965).

Primary Examiner—Werren B. Lone
Attorney, Agent, or Firm—Mark A. Montgomery

[57] ABSTRACT

A process for producing dimeric unsaturated aldehydes from alpha, beta unsaturated aldehyde is disclosed. This process is conducted by contacting the alpha, beta unsaturated aldehyde with a copper (II) catalyst and a complexing amine catalyst in a medium with a relatively high dielectric constant in substantially anhydrous and aprotic conditions.

18 Claims, No Drawings

OXIDATIVE COUPLING OF ALPHA, BETA UNSATURATED ALDEHYDES

FIELD OF THE INVENTION

The present invention relates to a process for the production of dimeric unsaturated aldehydes. The present invention more particularly relates to the process of preparing dimeric unsaturated aldehydes by oxidatively coupling alpha, beta unsaturated aldehydes.

BACKGROUND OF THE INVENTION

Dimeric unsaturated aldehydes could be very useful in many applications if they could be produced economically. Dimeric unsaturated aldehydes can be used as a starting material for many useful products. One group of products are glycols that can be used for the preparation of polyesters. The resulting glycols are flexible and can be produced by reducing the dimeric unsaturated aldehydes. The polyesters produced from glycols with large aliphatic side groups produce flexible polymers with low glass transition temperatures. Flexible glycols and glycols with large side chains act as their own plasticizing agent when incorporated into a polyester.

Dimeric unsaturated aldehydes could also find a use in the production of polyurethanes and nylons by reductive amination to produce flexible diamine monomers.

The dimeric unsaturated aldehydes are also useful for preparing diacrylates or dicarboxylates. The diacrylates could function as property modifiers for acrylic resins. The dicarboxylates could be used as the diacid component of polyester.

Although dimeric unsaturated aldehydes could find uses in many applications their production is relatively costly, thus limiting their current use. Dimeric unsaturated aldehydes are generally prepared by condensing an allylically halogenated aldehyde with the corresponding allylic unsaturated aldehyde carbanion. However, allylically halogenating the unsaturated aldehyde and making the unsaturated aldeyde carbanion are both very costly, and furthermore combining these two intermediates produce the desired product plus a stoichiometric amount of salt, the disposal of which is difficult. Another method of producing dimeric unsaturated aldehydes entails the dehydrohalogenation of dihalodihalides, which in turn come from the hydrofomylation of divinyldihalides. As with the above process, this process is expensive and produces salt.

It would be very desirable to be able to produce dimeric unsaturated aldehydes from an inexpensive starting material at high yields and high conversion by an inexpensive process avoiding the high cost and pollution problems of the prior art.

It is known that copper catalysts form ketones from conjugated unsaturated aldehydes containing methylene groups (Rec. Trav. Chim., 84, 1203 (1965). Copper catalysts are also known to oxidatively cleave electron rich aromatic phenols and amines to muconic acid (Tetr., 34, 641 (1978). Copper, pyridine catalysts are also known to effect the oxidative coupling of terminal alkynes (Org. Snyth. Coll. Vol. V, 517 (1973) and J. Amer. Chem. Soc., 99, 1487 (1977).

It is also known that the coupling of ketones with copper catalyst requires extensive substitution with cyano and aromatic groups to stabilize the intermediate oxidation product (J. Org. Chem., 36, 3160, (1971). It is known that homoconjugated unsaturated ketones are oxidatively coupled with copper, pyridine, methanol catalyst (Rec. Trav. Chim., 84, 1233 (1965).

SUMMARY OF THE INVENTION

The process according to the present invention for producing dimeric unsaturated aldehydes comprises:

(a) contacting an alpha, beta unsaturated aldehyde with a copper (II) catalyst and a complexing amine catalyst in a medium with a relatively high dielectric constant in substantially anhydrous and aprotic conditions; and (b) recovering the oxidatively dimerized product of said alpha, beta unsaturated aldehyde.

DETAILED DESCRIPTION OF INVENTION

The applicant has unexpectedly discovered an economical process of producing dimeric unsaturated aldehydes from alpha, beta unsaturated aldehydes using a copper (II) catalyst at high conversion and high yields. This is particularly unexpected since known related catalysts such as copper/amine in methanol or water give no reaction.

The production of the dimeric unsaturated aldehydes according to the present invention comprises contacting an alpha, beta unsaturated aldehyde with a copper (II) catalyst and a complexing amine catalyst in a medium with a relatively high dielectric constant in substantially anhydrous and aprotic conditions. The reaction is thought to take place through a series of steps as shown in Scheme I and Scheme II.

SCHEME I

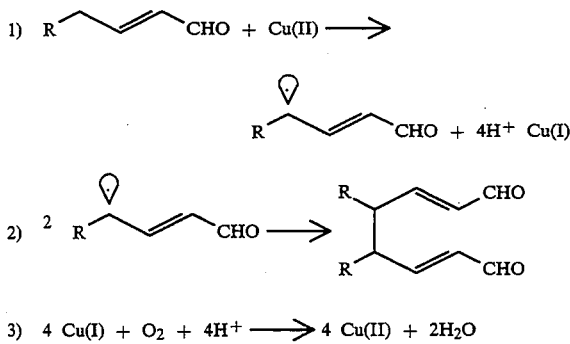

3) $4\ Cu(I) + O_2 + 4H^+ \longrightarrow 4\ Cu(II) + 2H_2O$

SCHEME II

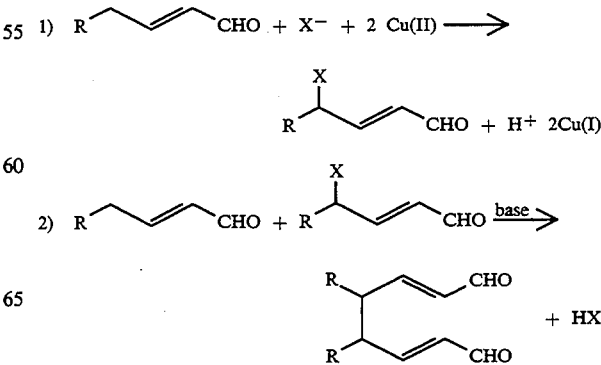

-continued
SCHEME II

3) $4 Cu(I) + O_2 + 4H^+ \longrightarrow 4 Cu(II) + 2 H_2O$

In both schemes the actual product shown in Step 2 is a mixture of isomers rather than the single product depicted. In both schemes, Step 1 is usually the slow step. Using inappropriate solvents occasionally causes step 2 in Scheme II to become the slow step. But in both cases, Step 3 is fast. In Scheme II X is a hydroxide hydroperoxide or the counter anion of the copper (II) catalyst such as a halide.

The process according to the present invention can generally be conducted at any temperature below the decomposition point of any component in the reaction mixture. This temperature, however, is preferably between 0° and 100° C., more preferably about 20° to 80° C. with a temperature of about 40° to 60° C. being most preferred. At temperatures much above 100° C. the reaction is very fast but side reactions cause lower yields and the copper (II) catalyst rapidly looses activity. Whereas temperatures much below 0° C., the reaction process is relatively slow.

The reaction process of the present invention can generally be conducted at any pressure so long as the reactants are in the liquid phase. The reaction process preferably is conducted at a partial oxygen pressure of about 0.0001 atmospheres to about 10 atmospheres, more preferably about 0.2 to 1 atmosphere with a partial oxygen pressure of about ambient pressure being most preferred. The reaction rates at a partial oxygen pressure much below about 0.0001 atmospheres are generally too slow to be useful. Whereas a partial oxygen pressure much above 10 atmospheres does not significantly increase the reaction rate because the function of oxygen is to oxidize copper (I) to copper (II), as shown in step 3 in schemes I and II above. The presence of oxygen does not affect any of the slow (rate determining) steps. In fact, a very high oxygen presence is potentially dangerous if intermediate hydroperoxy and peroxy derivatives of the organic substrate get to dangerously high levels.

The process according to the present invention is generally conducted in a stirred anaerobic reactor with a closed solvent evaporation and reoxidizing slip stream loop. This apparatus generally removes water produced in the reaction and reoxidizes copper (I) to copper (II) catalyst. Suitable examples of such an apparatus include glass lined tanks, metal tanks, and tubular pumped around reactors with agitation being provided by stirring, pumps, gas sparging, or shaking.

The process according to the present invention is conducted in substantially anhydrous conditions. This means that the water content during the reaction is generally below about 10 wt. %, more preferably below about 2 wt. % with a wt. % of water below about 1 being most preferred. Water is generated during the reaction in the presence of oxygen during the oxidation of copper (I) salts to copper (II) salts. After a period of time water must be removed for the reaction to continue at a reasonable rate since water competes with reactive sites on the catalyst, slowing down the reaction, and in high amounts causes the catalyst to precipitate. Water contents much above about 10 % slow down the reaction to undetectable rates. Whereas water concentrations much below about 1% are not economically attainable nor needed since the reaction proceeds at a relatively high rate at moderately low concentrations of water.

Water can be removed from the reaction mixture by any number of known methods, however, it is preferred to continuously remove the water by azeotropic distillation of a slip stream from the reaction mixture, thus continuously removing a portion of the water during the reaction. This is preferably conducted using an added azeotropic agent which causes water in the distillate to separate for disposal. An alternative method of removing the water entails filtering off the solid catalyst and then dehydrating it in a stream of hot gas.

The reactant used in the dimerization reaction of the present invention is preferably an alpha beta unsaturated aldehyde of the formula:

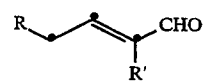

wherein R and R' are independently selected from hydrogen and aliphatic and aromatic hydrocarbon radicals, preferably having from 1 to 20 carbon atoms, more preferably 1 to 4. Suitable examples of alpha, beta unsaturated aldehydes include crotonaldehyde, 2-methyl-2-propenal, 2-ethyl-2-hexenal, 2-propyl-2-octenal, 2,4-diphenyl-2-butenal and the like and mixtures thereof. These alpha, beta unsaturated aldehydes are generally produced from aldol condensation of linear saturated aldehydes.

The most preferred alpha, beta unsaturated aldehydes due to availability, ease in handling, reactivity, and useful dimerized products are crotonaldehyde, and 2-ethyl-2-hexenal.

The dimerized product of said alpha, beta unsaturated aldehyde is generally a mixture of dimerized products and can be a mixture of the following formulae;

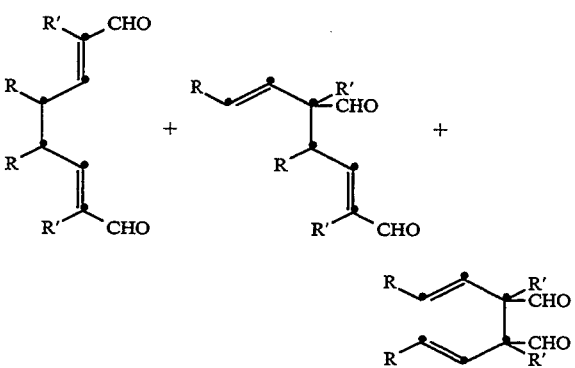

wherein R and R' are independently selected from hydrogen and aliphatic and aromatic hydrocarbon radicals.

Examples of oxidatively dimerized products of the alpha, beta unsaturated aldehydes include dehydrodicrotonaldehyde and dehydrodi(2-ethylhexenal).

The concentration of the copper (II) catalyst present during the dimerization reaction of step (a) is equal to about 0.0001 to 100 mole % of the alpha, beta unsaturated aldehyde, more preferably about 1 to 100 mole % with an amount of copper (II) catalyst equal to about 3 to 10 mole % of said alpha, beta unsaturated aldehyde being most preferred.

The copper catalyst used in the reaction of the present invention is only reactive when it is in the copper (II) oxidation state and must be oxidized from the copper (I) oxidation state to the copper (II) oxidation state after completing its part in the oxidative dimerization of the alpha, beta unsaturated aldehyde. This oxidation of the copper catalyst is preferably done continuously in the presence of an oxygen containing gas such as air with the partial oxygen pressure as stated above. A stepwise oxidation also works, with a corresponding small decline in the overall reaction rate since the slow rate determining steps take place in the absence of oxygen. The copper (II) form of the copper catalyst is preferably at least partially soluble so as to have a substantial amount of the copper (II) catalyst in contact with the alpha, beta unsaturated aldehyde reactant during the reaction. The copper (II) catalyst is preferably a soluble copper (II) salt wherein the counter ion for the copper is such that it permits easy dehydration of hydrated copper species, does not strongly complex to copper to limit solubility, and readily displaces from intermediates made with the alpha, beta unsaturated aldehyde. The counter ion for the copper is preferably selected from the group consisting of fluoride, chloride, bromide, nitrates, sulfates and carboxylates, with chloride and bromide being most preferred. Suitable examples of counter ion nitrates include copper (II) nitrate hexahydrate, copper (II) nitrate trihydrate. Suitable examples of counter ion sulfates include copper (I) sulfate, copper (II) sulfate, copper (II) sulfate pentahydrate, and $CuSO_4 \cdot 3Cu(OH)_2$. Suitable examples of counter ion carboxylates include aliphatic, carboxylic or polycarboxylic acids and aromatic carboxylic or polycarboxylic acids such as formate, acetate, propionate, butyrate, and benzoate.

The complexing amine catalysts used in the reaction in contacting step (a) can include any anhydrous amine that is also a good complexing agent. The complexing amine catalyst is important for several reasons (1) the organic character of the amine promotes contact between the complexed catalyst and the organic substrate; (2) the amine complexes the copper catalyst changing its oxidation reduction/potential; and (3) the amine scavenges copper catalyst at the end of the reaction forming a crystalline complex recoverable by filtration. The amine also deprotonates the organic substrate giving the most readily oxidizable organic species so a strong base character, in addition to the strong complexing character is important. The pKb of the complexing amine catalyst is preferably below 9 more preferably below 3.

The molar concentration of the complexing amine catalyst is preferably at least as high as the copper (II) catalyst. This molar concentration is more preferably at a molar ratio range of amine to copper of about 1:1 to 10:1 with a molar ratio range of amine to copper of 2:1 to 6:1 being most preferred. At a molar concentration ratio of complexing amine catalyst to copper (II) catalyst much above 3:1 the excess complexing amine catalyst acts as a cosolvent.

The suitable complexing amine catalysts that meet the requirements above include pyridine, derivatives of pyridine, bipyridyl, derivatives of bipyridyl, trimethylamine, triethylamine, tripropyl-amine, tributylamine, 1,4-diazabicyclo-[2,2,2]-octane, N,N,N,N-tetramethyl-1,2-ethylenediamine, N,N-dimethylpiperazine, N,N,N,N-pentamethyldiethylene-triamine, dimethylamine, diethylamine, dipropylamine, dibutylamine, pyrrolidine, piperidine, methylamine, ethylamine, propyamine, aniline, and aniline derivatives. The more preferred complexing amine catalysts are selected from tertiary amines. The most preferred complexing amine catalysts, due to high product yield and ease in catalyst recovery, are 1,4-diazabicyclo-[2,2,2]-octane and N,N,N,N-tetramethyl-1,2-ethylenediamine.

The oxidative dimerization reaction is conducted in a medium with a relatively high dielectric constant in substantially anhydrous and aprotic conditions. The term relatively high dielectric constant generally means $\epsilon$ is greater than about 40. This generally results from the use of a solution that has a high concentration of a solvent with a very high dielectric constant and is generally in the presence of a solvent and co-solvent. The complexing amine catalyst or alpha, beta unsaturated aldehyde reactant can act as a co-solvent but an aprotic solvent is generally needed.

Substantially anhydrous and aprotic conditions means that the reaction in contacting step (a) is preferably conducted in the presence of a medium that includes an anhydrous polar aprotic solvent. Examples of suitable anhydrous polar aprotic solvents include N-methylpyrrolidone (NMP), dimethylsulfoxide (DMSO), hexamethylphosphorous-triamide (HMPT or HMPA), and dimethylformamide (DMF), with DMF being the most preferred. These anhydrous polar aprotic solvents are generally preferred due to their high dielectric constant or polarity and are generally in the concentration of about 1 to 90 wt. % of the total weight of the components in contacting step (a). More preferably 5 to 50 wt. %, with a total wt. % of about 15 to 30 being most preferred.

After the reaction that is conducted in the contacting step (a) the copper catalyst is recovered generally by filtering an insoluble complex of the copper catalyst and the complexing amine catalyst. This is generally done by filtering a slipstream.

The recovered oxidatively dimerized product can further be reacted to form other useful products. Examples of these include oxidizing to form bis-acrylic acids, reducing to form flexible glycols used for the production of polyesters, reductively aminating to form flexible diamines, and partially reducing to form bisaldehyds.

The following examples are intended to illustrate the present invention but are not intended to limit the reasonable scope thereof.

EXAMPLE 1

The charge to a 500 milliliter round bottom flask equipped with a thermometer, a gas inlet, and a magnetic stirring bar was 10.2 grams copper (II) chloride dihydrate (59.8 millimoles). The contents were heated while being stirred to 160 C in a slow stream of nitrogen which dehydrated the bluegreen-hydrate to yellow-brown anhydrous material over two hours (containing less than 1% water). After cooling this material to room temperature, 100 milliliters of anhydrous dimethylformamide was added followed after dissolution by 37 milliliters of anhydrous N,N,N,N-tetramethyl-1,2-ethylenediamine, (TMEDA 28.5 grams, 245.3 millimoles) and 100 milliliters of 2-ethyl-2-hexenal (82.5 grams, 654 millimoles) completing the ingredients needed for the reaction. This mixture formed a blue complex. The amine:copper ratio was 4.1:1 and the substrate:copper ratio was 10.9:1.

The initially formed blue complex faded to a brown solution as the reaction progressed at room temperature and the copper (II) complex changed to copper (I). Accompanying the change in the copper complex, several dimeric organic compounds with molecular weights twice that of 2-ethyl-2-hexenal minus two (i.e. 250) appeared. Without adding oxygen, the reaction stopped and no further product appeared. With added oxygen, the brown color changed to blue-green and more product appeared. This cycle repeated as long as organic substrate remained although the catalyst darkened in color as the reaction produced water. The time needed for 94 percent conversion of the starting material was 500 hours.

The workup consisted of filtering off the catalyst and washing the solvent and excess amine out with water and dilute hydrochloric acid. The recovery of solid catalyst was 11.4 grams (49.5 percent based on Cu(TMEDA)$_2$.H$_2$O).Cl$_2$). The yield of a mix of dimeric isomers based on gas chromatographic analysis was 97.4 percent of starting material consumed.

EXAMPLE 2

This example was conducted according to Example 1 except that three times as much TMEDA co-catalyst was used. This example produced a mix of oxidative dimers in 96.8 percent yield based on 93.0 percent conversion in 250 hours at room temperature.

This example shows the effect of co-catalyst concentration on the reaction rate.

EXAMPLE 3

This example was conducted according to Example 1 except that 1,4-diazabicyclo-[2,2,2]-octane (DABCO) was used instead of TMEDA. This example produced the mix of oxidatively dimerized product in 96.5 percent yield based on a conversion of 92.1 percent in 500 hours at room temperature. The catalyst recovery at the end of the reaction was 85.7 percent (based on Cu(DABCO)$_2$.H$_2$O.Cl$_2$).

This example shows the use of different anhydrous tertiary amines to catalyze the oxidative coupling.

EXAMPLE 4

This example was conducted according to Example 1 except that pyridine was used instead of TMEDA. This example produced the mix of oxidatively dimerized product in 94.5 percent yield based on a conversion of 87.8 percent in 1500 hours.

This example shows the use of anhydrous aromatic amines to catalyze the oxidative coupling.

EXAMPLE 5

This example was conducted according to Example 1 except that piperidine was used instead of TMEDA. This example produced the mix of oxidatively dimerized product in 83.6 percent yield based on a 53.6 percent conversion in 1000 hours. The catalyst recovery at the end of the reaction was 62.0 percent (based on Cu(piperidine)$_2$.H$_2$O.Cl$_2$).

This example shows the use of anhydrous secondary amines to catalyze the oxidative coupling.

EXAMPLE 6

This example was conducted according to Example 1 except that anhydrous copper (II) acetate was used instead of anhydrous copper (II) chloride. This example produced the mix of oxidatively dimerized product in 79.8 percent yield based on a 4.6 percent conversion of starting material in 1500 hours.

This example shows the use of different copper salts to catalyze the oxidative coupling.

EXAMPLE 7

This example was conducted according to Example 1 except that anhydrous copper (II) bromide was used instead of anhydrous copper (II) chloride. This example produced the mix of oxidatively dimerized product in 95.8 percent yield based on an 84.9 percent conversion in 500 hours.

This example shows the use of different copper salts to catalyze the oxidative coupling.

EXAMPLE 8

This example was conducted according to Example 1 except that the dimethylformamide solvent was omitted and the amount of TMEDA was tripled. This example produced no oxidative dimer in 1000 hours. It did produce in 87.3 percent yield and 12.0 percent conversion monochloro-2-ethyl-2-hexenal and monohydroxy-2-ethyl-2-hexenal. Adding dimethylformamide solvent at this point caused the reaction to proceed to oxidative dimers including turning both monochloro-2-ethyl-2-hexenal and monohydroxy-2-ethyl-2-hexenal into these products.

This example shows two things. The reaction needs a solvent with a high dielectric constant to proceed normally. And the reaction produces oxidized intermediates which react with unoxidized starting material to produce oxidative dimers.

EXAMPLE 9

This example was conducted according to Example 1 except that the reaction was completed at 46 C. This example produced the mix of oxidative dimers in 97.1 percent yield based on 91.9 percent conversion of starting material in 150 hours.

This example shows the effects of changing conditions on the reaction rate.

EXAMPLE 10

This example was conducted according to Example 1 except that anhydrous crotonaldehyde was used instead of 2-ethyl-2-hexenal as the feed/substrate and the temperature was 0 C instead of ambient. This example produced the mix of oxidative dimers in 78.8 percent yield based on a 76.9 percent conversion in 25 hours. The remaining 23.1 percent of the product appeared to be mainly aldol condensation product.

This example shows generality of this reaction by the use of different substrates.

EXAMPLE 11

The materials charged into a 500 milliliter round bottom flask equipped with a magnetic stirring bar included 100 milliliters of the dry homoconjugated substrate isomesityl oxide (4-methyl-4-pentene-2-one) (0.87 mole), 8.8 grams anhydrous copper (II) chloride (66 millimoles), 20 milliliters TMEDA, 100 milliliters anhydrous pyridine, and 100 milliliters anhydrous methanol. The reaction was essentially complete within three days producing unsaturated $C_{12}$ diketone isomers in 90 % yield. In this example dry air kept the copper in its +2 oxidation state.

EXAMPLE 12

This example was conducted according to Example 11 except that 2-ethyl-2-hexenal (0.65 mole) was substituted for the homoconjugated substrate isomesityl oxide (4-methyl-4-pentene-2-one). Stirring this mixture at ambient temperatures gave no reaction even after four months.

This example shows the effect of adding polar aprotic solvents to the reaction mixture.

This example in view of Example 11 shows that conditions for oxidatively coupling of homoconjugated unsaturated ketones do not work with conjugated unsaturated aldehydes.

I claim:

1. A process for producing dimeric unsaturated aldehydes comprising:
   (a) contacting an alpha, beta unsaturated aldehyde with a copper (II) catalyst and a complexing amine catalyst in a medium with a relatively high dielectric constant in substantially anhydrous and aprotic conditions; and
   (b) recovering the oxidatively dimerized product of said alpha, beta unsaturated aldehyde.

2. The process according to claim 1 wherein said contacting is at a temperature of about 0° C. to 100° C.

3. The process according to claim 1 wherein said contacting is at a partial oxygen pressure of about 0.2 to one atmosphere.

4. The process according to claim 1 wherein the concentration of water during said contacting is below about 10 wt %.

5. The process according to claim 1 wherein water is removed by a slip stream from the reaction mixture during said contacting.

6. The process according to claim 1 wherein said alpha, beta unsaturated aldehyde is of the formula;

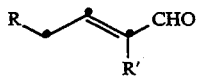

wherein R and R' are independently selected from hydrogen and aliphatic and aromatic hydrocarbon radicals.

7. The process according to claim 6 wherein said alpha, beta unsaturated aldehyde is selected from the group consisting of crotonaldehyde, 2-methyl-2-propenal, 2-ethyl-2-hexenal, 2-propyl-2-octenal, 2,4-diphenyl-2-butenal and mixtures thereof.

8. The process according to claim 1 wherein the concentration of said copper (II) catalyst at the beginning of step (a) is equal to about 0.0001 to 100 mole percent of said alpha, beta unsaturated aldehyde.

9. The process according to claim 1 wherein said copper (II) catalyst is a copper (II) salt and wherein the counter ion for copper is such that it permits easy dehydration of hydrated copper species, does not strongly complex to copper to limit its solubility, and readily displaces from intermediates made with said alpha, beta unsaturated aldehydes.

10. The process according to claim 9 wherein said counter ion is selected from the group consisting of fluoride, chloride, bromide, nitrates, sulfates and carboxylates.

11. The process according to claim 10 wherein said copper (II) catalyst is copper (II) chloride.

12. The process according to claim 1 wherein said complexing amine catalyst is a tertiary amine.

13. The process according to claim 1 wherein said complexing amine catalyst is selected from the group consisting of pyridine, derivatives of pyridine, bipyridyl, derivatives of bipyridyl, trimethylamine, triethylamine, tripropyl-amine, tributylamine, 1,4-diaza-[2,2,2]-bicyclooctane, N,N,N,N-tetramethyl-1,2-ethylenediamine, N,N-dimethylpiperazine, N,N,N,N,N-pentamethyldiethylene-triamine, dimethylamine, diethylamine, dipropylamine, dibutylamine, pyrrolidine, piperidine, methylamine, ethylamine, propyamine, aniline, and aniline derivatives.

14. The process according to claim 1 wherein said complexing amine catalyst is in a molar concentration that is at least as high as the copper (II) catalyst.

15. The process according to claim 1 wherein said medium contains an anhydrous polar aprotic solvent.

16. The process according to claim 15 wherein said anhydrous polar aprotic solvent is selected from the group consisting of N-methylpyrrolidone, hexamethylphosphorous-triamide and dimethylformamide.

17. The process according to claim 15 wherein the concentration of said anhydrous polar aprotic solvent is about 5 to 50% of the total weight of the components in step (a).

18. The process according to claim 1 wherein the copper (II) catalyst is recovered after step (a) by filtering the insoluble complex of copper catalyst and complexing amine catalyst.

* * * * *